United States Patent
Takiguchi (10) Patent No.: US 8,625,087 B2
(45) Date of Patent: Jan. 7, 2014

(54) PACKING CONTAINER, METHOD OF PACKING OPTICAL PROBE, LASER SYSTEM, AND CHECKING METHOD

(75) Inventor: Yoshiro Takiguchi, Tokyo (JP)

(73) Assignee: Sony Corporation, Tokyo (JP)

(*) Notice: Subject to any disclaimer, the term of this patent is extended or adjusted under 35 U.S.C. 154(b) by 94 days.

(21) Appl. No.: 13/285,704

(22) Filed: Oct. 31, 2011

(65) Prior Publication Data
US 2012/0113414 A1 May 10, 2012

(30) Foreign Application Priority Data

Nov. 8, 2010 (JP) .................................. 2010-250153

(51) Int. Cl.
| | |
|---|---|
| G01J 1/00 | (2006.01) |
| G01J 1/04 | (2006.01) |
| G01J 4/00 | (2006.01) |
| A61B 5/00 | (2006.01) |
| H01J 3/14 | (2006.01) |

(52) U.S. Cl.
USPC ............... 356/213; 385/12; 385/13; 600/310; 600/314; 600/315; 600/316; 600/322; 600/323; 600/325; 600/326; 600/327; 250/216; 250/227.14; 250/227.19

(58) Field of Classification Search
USPC ............... 356/213; 385/12, 13; 600/310–334; 372/29.01, 29.021, 38.1, 38.01–38.09; 250/216, 227.11, 227.14, 227.19, 218
See application file for complete search history.

(56) References Cited

U.S. PATENT DOCUMENTS

| | | | |
|---|---|---|---|
| 4,677,531 | A | 6/1987 | Szeles |
| 4,914,284 | A | 4/1990 | Halldorsson et al. |
| 5,029,957 | A | 7/1991 | Hood |
| 5,042,894 | A | 8/1991 | Swemer |
| 5,217,290 | A | 6/1993 | Windross |
| 5,929,989 | A * | 7/1999 | Mori et al. .................... 356/477 |
| 6,334,716 | B1 * | 1/2002 | Ojima et al. .................... 385/89 |
| 2009/0105082 | A1 * | 4/2009 | Chetverin et al. ................. 506/7 |
| 2010/0221816 | A1 * | 9/2010 | Hanafusa et al. .......... 435/287.2 |

FOREIGN PATENT DOCUMENTS

EP   1626299   2/2006

OTHER PUBLICATIONS

European Patent Office, Partial European Search Report, issued in connection with European Patent Application Serial No. 11008278.1, dated Feb. 23, 2012. (7 pages).
European Search Report issued Jun. 25, 2012, corresponding to European Appln. No. 11008278.1.

* cited by examiner

*Primary Examiner* — Hoa Pham
*Assistant Examiner* — Sunghee Y Gray
(74) *Attorney, Agent, or Firm* — K&L Gates LLP (57) ABSTRACT

Disclosed herein is a packing container including: a packing container body including a leading-out section which contains an optical probe having a first end section for incoming of a laser beam and a second end section for outgoing of the incoming laser beam, which leads out the first end section of the optical probe thus contained to the exterior and which is sealed, and a window section by which the laser beam going out from the second end section of the contained optical probe is led out to the exterior; and a light-transmitting member which closes the window section and permits the laser beam to pass therethrough.

7 Claims, 11 Drawing Sheets

PACKING CONTAINER, METHOD OF PACKING OPTICAL PROBE, LASER SYSTEM, AND CHECKING METHOD

CROSS REFERENCES TO RELATED APPLICATIONS

The present application claims priority to Japanese Patent Application No. 2010-250153 filed on Nov. 8, 2010, the disclosure of which is incorporated herein by reference.

BACKGROUND

The present disclosure relates to a packing container for packing an optical probe and a method of packing an optical probe, and also relates to a laser system and a checking method which use such a packing container.

In recent years, applications and researches of insertion into a blood vessel of an optical probe having a beam outgoing section at the tip thereof have come to be made. Since the optical probe is inserted into a blood vessel, its cleanliness (sanitariness) should be extremely higher than in the other uses in the past. It is also important to control the output intensity of a laser beam let go out from a beam outgoing section of the optical probe.

In use of such an optical probe, a beam incoming section of the optical probe is attached to a beam output port of a laser system, and the tip of the optical probe is inserted into a blood vessel. The laser system is provided with an optical power meter for measuring the output intensity of the laser beam outputted from the beam outgoing section of the optical probe. Before use, the operator bring the beam outgoing section of the optical probe close to the optical power meter, and checks the output intensity of the laser beam outputted from the beam outgoing section of the optical probe.

Since the optical power meter is not sterilized, it is strictly undesirable to bring the beam outgoing section of the optical probe into proximity to or contact with the optical power meter. In view of this, normally, the beam outgoing section of the optical probe is inserted in an applicator having undergone a sterilizing treatment, and is mounted to the optical power meter of the laser system through the applicator.

SUMMARY

The beam outgoing section of the optical probe may be brought into proximity to or contact with a filthy region of the laser system due to an operator's misoperation or the like. In addition, the applicator should be sterilized each time it is put to use, which worsens workability.

Thus, it is desirable to provide a packing container, a method of packing an optical probe, a laser system, and a checking method by which the output intensity of a laser beam can be checked while securing cleanliness (hygiene) and without spoiling workability.

A packing container according to an embodiment of the present technology has a packing container body and a light-transmitting member.

The packing container body includes a leading-out section which contains an optical probe having a first end section for incoming of a laser beam and a second end section for outgoing of the incoming laser beam, which leads out the first end section of the optical probe thus contained to the exterior and which is sealed, and a window section by which the laser beam going out from the second end section of the contained optical probe is led out to the exterior. The packing container body is preferably has air-tightness in such an extent that the cleanliness (sanitariness) of the sterilized optical probe can be secured.

The light-transmitting member is for closing the window section therewith, and has a member which permits the laser light to pass therethrough.

In this configuration, the laser beam let go out from the second end section is led to the exterior through the window section closed with the light-transmitting member. Therefore, during measurement of the laser beam, the second end section is prevented from being brought into proximity to or contact with the laser system or the like which constitutes a filthy region. In addition, the need for an applicator or the like is eliminated. Accordingly, the checking of the output intensity of the laser beam can be carried out while securing cleanliness reliably and without spoiling workability.

In a packing container according to an embodiment of the present technology, the packing container body includes an optical probe containing box which has an open side and which is provided with the leading-out section and the window section, and a film member which closes the open side.

In this configuration, the optical probe can be contained into the containing box through the open side, and the open side can be closed with the film member. Therefore, the optical probe can be easily contained into the packing container, and can be easily taken out of the packing container by breaking the film member. In addition, the form of the containing box ensures that at the time of secondary packing, a multiplicity of the packing containers can be stackedly contained into a corrugated fiberboard box or the like.

In a packing container according to an embodiment of the present technology, the optical probe containing box has a first surface provided with a positioning section for positioning of both the window section and an optical power meter of a laser system to which the window section and the packing container are mounted.

In this configuration, the window section is provided at the same surface as that for the positioning section for positioning in relation to the optical power meter of the laser system to which the packing container is mounted. Therefore, on the laser system side, also, the optical power meter can be set on the same surface on which the positioning section is disposed. Accordingly, checking of the output intensity of the laser beam and the like can be carried out with the components in a stably held state. Moreover, the configuration on the laser system side can be simplified.

In a packing container according to an embodiment of the present technology, the optical probe containing box has a second surface which is opposed to the first surface and which is provided with the leading-out section at a position corresponding to the window section.

In this configuration, the window section and the leading-out section are provided on the opposed surfaces and at the corresponding positions. Therefore, the optical probe can be contained in the packing container in such a manner that when the optical probe is contained in the packing container in a looped state, the optical probe is prevented from being crooked, and that when the packing container is mounted to the laser system, the first end section led out through the leading-out section does not interfere with the laser system.

In a method of packing an optical probe according to an embodiment of the present technology, the optical probe is contained in a containing box which has an open side, a leading-out section, and a window section closed with a light-transmitting member permitting the laser beam to pass therethrough. In this instance, the optical probe having a first end section for incoming of a laser beam and a second end section for outgoing of the incoming laser beam is contained in the containing box in such a manner that the first end section is led out to the exterior through the leading-out section and that the second end section is opposed to the window section with a predetermined spacing therebetween. Next, the leading-out section is sealed with a sealing material, and the open side is closed with the film member.

In this configuration, the laser beam let go out from the second end section is led out to the exterior through the window section closed with the light-transmitting member. Therefore, at the time of checking the output intensity of the laser beam, the second end section is prevented from being brought into proximity to or contact with the laser system or the like which constitutes a filthy region. Accordingly, there is no need for an interface member such as an applicator. Consequently, the output intensity of the laser beam can be checked while securing cleanliness in an assured manner and without worsening workability.

A laser system according to an embodiment of the present technology includes a casing, an optical power meter, a positioning engaging section, and a checking unit.

The optical power meter is mounted to the casing, and receives the laser beam coming therein from a beam outgoing section of an optical probe kept contained in a packing container.

The positioning engaging section is provided on the casing at a position corresponding to a container-side engaging section provided on the packing container, in such a manner as to engage with the container-side engaging section, and determines the positional relationship between the beam outgoing section and the optical power meter.

The checking unit checks the output intensity of the laser beam coming in through the optical power meter.

In this configuration, when the container-side engaging section provided on the packing container is engaged with the positioning engaging section provided on the laser system, the beam outgoing section is positioned in a proper position in relation to the optical power meter. Therefore, the packing container can be fixed relative to the laser system as designed, independently of whether the operator is skilled or not. This ensures that checking of the output intensity of the laser beam can be carried out stably, independently of whether the operator is skilled or not.

In a checking method according to an embodiment of the present technology, a container-side engaging section provided on a packing container is put into engagement with a positioning engaging section provided on a laser system. Next, a laser beam coming from a beam outgoing section of an optical probe contained in the packing container is let in through an optical power meter of the laser system, the optical power meter being determined in positional relationship with the beam outgoing section of the optical probe by the engagement. Then, the output intensity of the laser beam coming in through the optical power meter is checked.

This ensures that the packing container can be fixed to the laser system as designed, independently of whether the operator is skilled or not. Consequently, the output intensity of the laser beam can be checked stably, independently of whether the operator is skilled or not.

In the above-mentioned configurations, the laser beam let go out from the second end section through the window section closed with the light-transmitting member is led out to the exterior. Therefore, the checking of the output intensity of the laser beam can be carried out while securing cleanliness (sanitariness) in a reliable manner and without spoiling workability.

Additional features and advantages are described herein, and will be apparent from the following Detailed Description and the figures.

DETAILED DESCRIPTION

Embodiments of the present application will be described below in detail with reference to the drawings.

FIGS. 1 to 5 illustrate the configuration of a packing container for an optical probe according to an embodiment of the present technology.

A packing container 1 shown in these figures includes a packing container body 10 and a light-transmitting member 30. An optical probe 40 to be contained in the packing container 1 has an optical probe body 41 having an optical fiber. The optical probe body 41 is provided, respectively at both ends thereof, with a beam incoming section 42 through which a laser beam is let come in and a beam outgoing section 43 through which the laser beam let come in via the beam incoming section 42 is let go out.

The packing container body 10 includes an optical probe containing box 11 and a film member 12.

The optical probe is, for example, an optical probe inserted in an endoscope or a catheter.

The optical probe containing box 11 is formed, for example, from a material selected from among COC (cyclic olefin copolymer), PC (polycarbonate), (HD)PE ((high-density) polyethylene), PET (polyethylene terephthalate), PS (polystyrene), etc., is, for example, rectangular in shape, and has an open side 13 on the upper side. The optical probe 40 is contained in the optical probe containing box 11 in the state of being looped in several turns. A first side surface 14 of the optical probe containing box 11 is provided with a leading-out section 15 through which the beam incoming section 42 of the optical probe 40 in a contained state is led out from the packing container 1 to the exterior, together with a part of the optical probe body 41. The leading-out section 15 is composed, for example, of a U-shaped notch formed from the upper end of the first side surface 14. The leading-out section 15 is provided at a position near one end of the first side surface 14. It suffices for the size of the leading-out section 15 to be, for example, slightly greater than the diameter of the optical probe body 41. After the beam incoming section 42 is led out from the packing container 1 to the exterior, the leading-out section 15 is sealed with a sealing material 16 composed, for example, of a UV-curing resin. The sealing may be conducted before or after the film member 12 is attached to the optical probe containing box 11.

A second side surface 17, opposed to the first side surface 14, of the optical probe containing box 11 is provided with a window section 18 and a positioning section 19.

The window section 18 is composed, for example, of a circular hole bored in the second side surface 17. The window section 18 is provided at a position (a position near one end of the second side surface 17) corresponding to the position of the leading-out section 15 provided in the first side surface 14. It suffices for the window section 18 to be so sized to ensure at least that the laser beam going out from the beam outgoing section 43 of the optical probe 40 contained in the packing container 1 can pass through the window section 18.

The positioning section 19 is for positioning in relation to an optical power meter (described later) of a laser system to which the packing container 1 is mounted. The positioning section 19 has recesses 19a, 19b provided respectively on both sides of the window section 18. Thus, the window section 18 is provided in the same surface as that in which the positioning section 19 is provided. The recesses 19a, 19b are engaged with positioning projections (described later) provided in the laser system. When the recesses 19a, 19b are engaged with the projections, the window section 18 is positioned in a proper position in relation to the optical power meter of the laser system.

The film member 12, for closing the open side 13, is formed from (LD)PE ((low-density) polyethylene), PC (polycarbonate), PET (polyethylene terephthalate) or the like which is thin and substantially transparent. The film member 12 is attached to the optical probe containing box 11 by fusing or by use of an adhesive. It suffices that the closure of the open side 13 with the film member 12 and the sealing of the leading-out section 15 with the sealing material 16 offer airtightness in such an extent that the cleanliness (sterility) of the optical probe 40 contained in the packing container 1 can be secured.

The light-transmitting member 30, for closing the window section 18, has a member permitting the laser beam to be pass therethrough. The light-transmitting member 30 is a flat plate-shaped member which is formed, for example, of COC (cyclic olefin copolymer), PC (polycarbonate), PET (polyethylene terephthalate), PS (polystyrene) or the like, and is adhered to the optical probe containing box 11 by use of an adhesive, for example.

Incidentally, a protective film of ETFE (tetrafluoroethylene-ethylene copolymer) or the like may be provided on the outside surface of the light-transmitting member 30, whereby marring of the light-transmitting member 30 due to friction with a secondary packing material (described later) can be prevented from occurring. Upon unsealing the secondary packing material, the ETFE film adhered to the window member is peeled off. For preventing the user from forgetting to peel off the ETFE film, it is recommendable that a part of the ETFE film adhered to the light-transmitting member 30 be bonded to the secondary packing material. In this case, simultaneously with unsealing of the secondary packing, the ETFE film is peeled off from the light-transmitting member 30.

Figure 1:
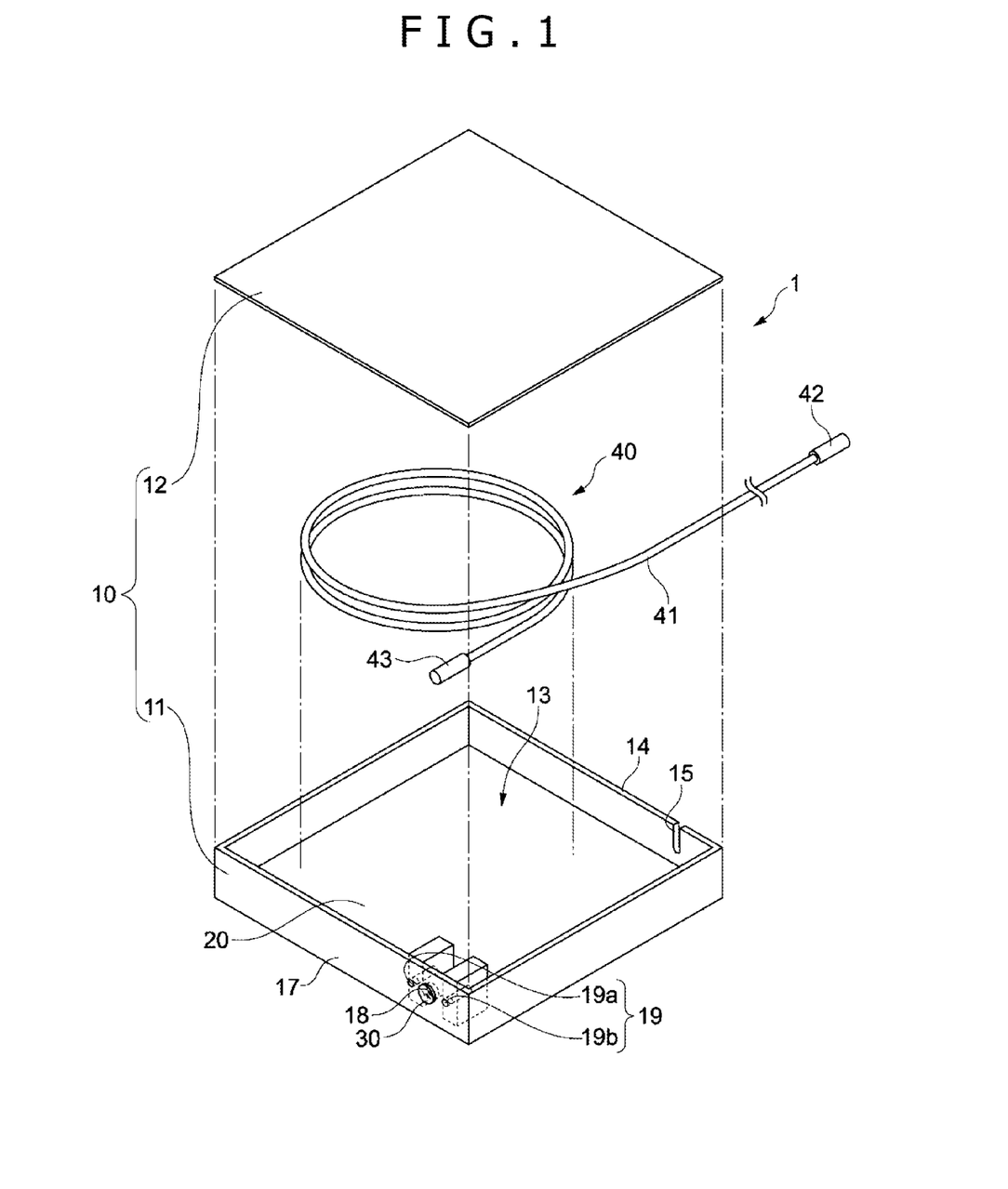
FIG. 1 is an exploded perspective view of showing the configuration of a packing container for an optical probe according to an embodiment of the present technology.
Figure 2:
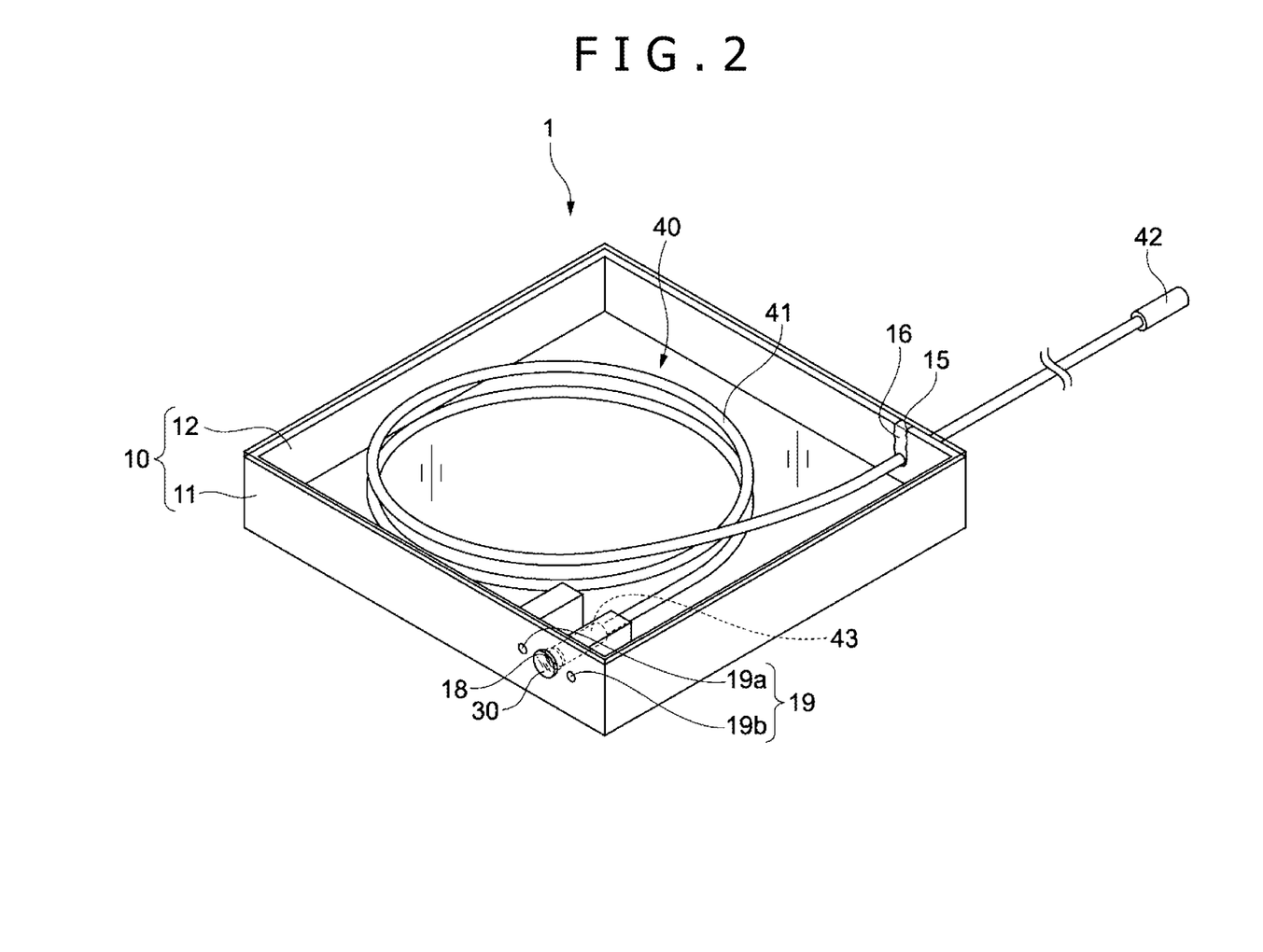
FIG. 2 is an assembly perspective view of FIG. 1.
Figure 3:
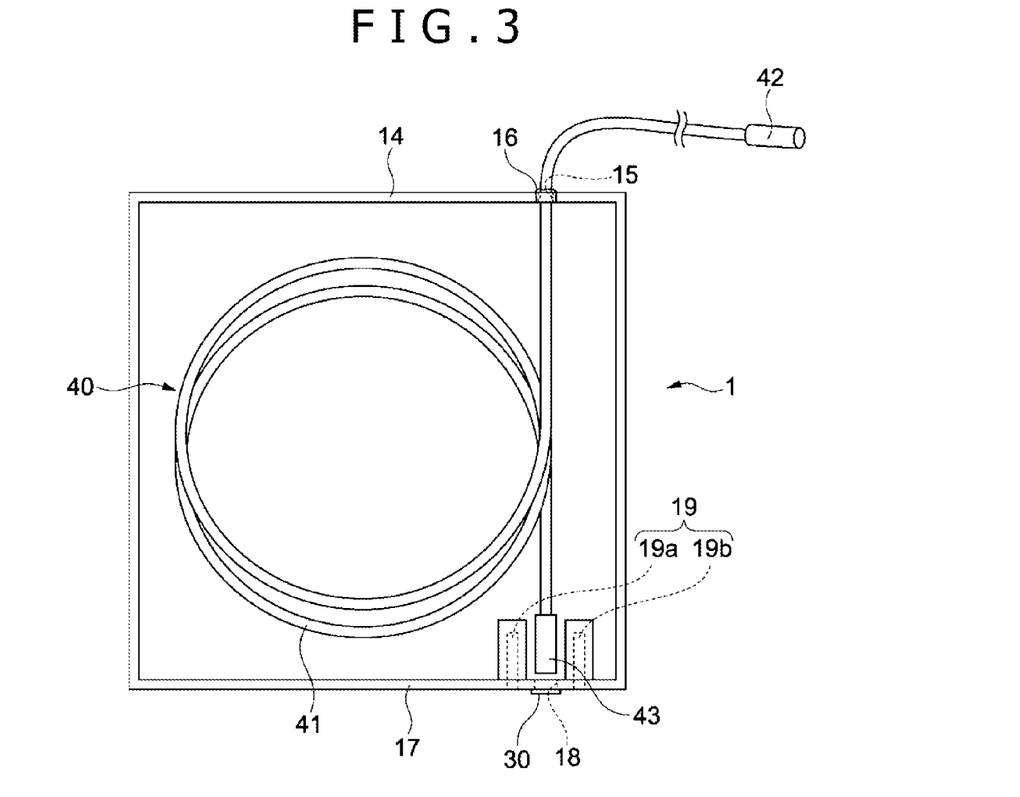
FIG. 3 is a plan view of FIG. 2.
Figure 4:
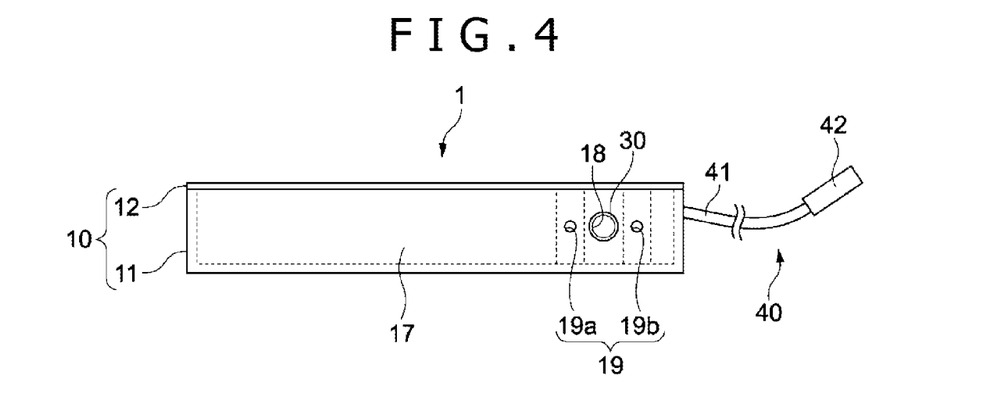
FIG. 4 is a front view of FIG. 2.
Figure 5:
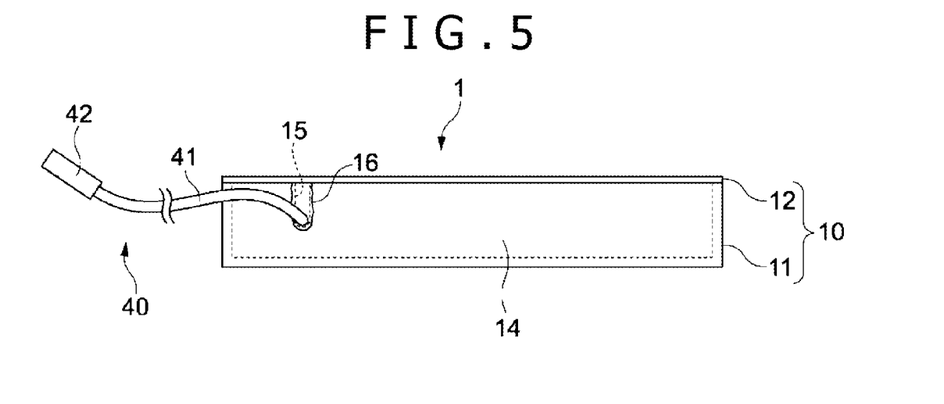
FIG. 5 is a back elevation of FIG. 2.
Figure 6:
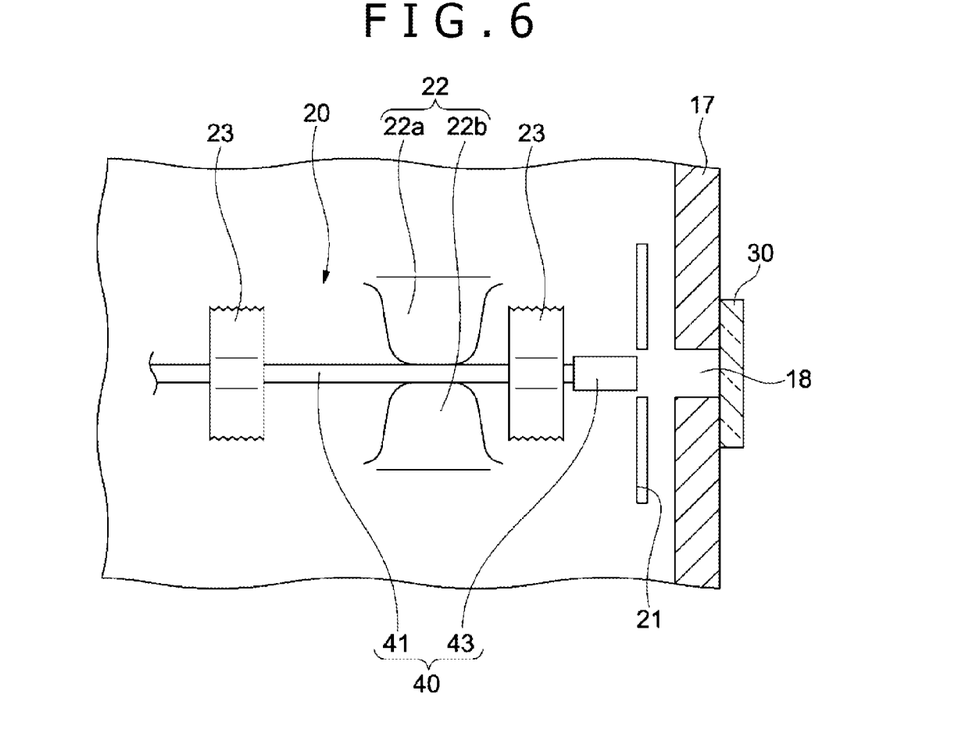
FIG. 6 is a partial enlarged plan view of FIG. 3.

FIG. 6 is an enlarged plan view of the light-transmitting member 30 and the surroundings thereof.

The beam outgoing section 43 of the optical probe 40 contained in the packing container 1 should be kept accurate in distance and angle in relation to the light-transmitting member 30 (the window section 18) (parallelism between the beam outgoing section 43 and the light-transmitting member 30). For ensuring this, therefore, for example, a floor surface 20 of the optical probe containing box 11 is provided with positioning grooves 21 and with a fixing section 22 for fixing that portion of the optical probe body 41 which is near the beam outgoing section 43. The fixing section 22 has, for example, a pair of projected sections 22a, 22b projected from the floor surface 20. The spacing between the projected sections 22a and 22b is so set that the optical probe body 41 can be clamped between the projected sections 22a, 22b.

The operator in charge of the packing with the packing container 1 positions the beam outgoing section 43 while relying on the positioning grooves 21, fixes the optical probe body 41 to the fixing section 22, and, further, fix the portions of the optical probe body 41 which are near the beam outgoing section 43 to the floor surface 20 of the optical probe containing box 11 by use of tape 23.

In an exemplary case, the diameter $R_1$ of the beam outgoing section 43 is 100 to 800 μm, the diameter $R_2$ of the window section 18 is 10 to 20 mm, the thickness t of the light-transmitting member 30 is 1 to 5 mm, and the distance L between the beam outgoing section 43 and the light-transmitting member 30 is 1 to 5 mm.

(Method of Packing Optical Probe)

Figure 7:
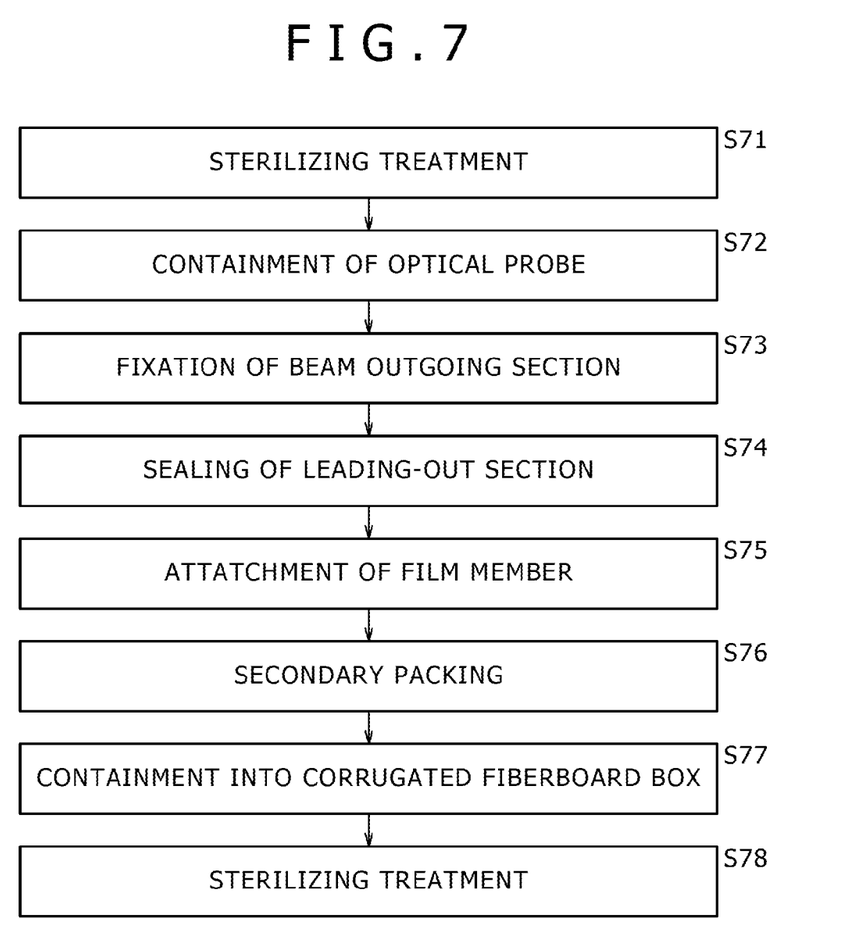
FIG. 7 is a flow chart showing a method of packing the optical probe shown in FIGS. 1 to 6.

Now, a method by which the optical probe 40 is packed in the packing container 1 configured as above will be described below, referring to FIG. 7.

First, the operator subject the optical probe 40 to a predetermined sterilizing treatment (step S71).

Next, the operator contains the optical probe 40 into the optical probe containing box 11 already equipped with the light-transmitting member 30 (step S72). In this instance, the operator leads out the beam incoming section 42 to the exterior through the leading-out section 15. In addition, as abovementioned, the operator positions the beam outgoing section 43 while relying on the positioning grooves 21, then fixes the optical probe body 41 to the fixing section 22, and fixes the portions near the beam outgoing section 43 of the optical probe body 41 to the floor surface 20 of the optical probe containing box 11 by the tape 23 (step S73).

Subsequently, the operator closes the leading-out section 15 by coating it with the sealing material 16 composed of a UV-curing resin, and cures the sealing material 16 by irradiation with UV rays, thereby to seal the leading-out section 15 (step S74).

Next, the operator covers the open side 13 with the film member 12, and attaches the film member 12 to the optical probe containing box 11 by fusing, whereby the open side 13 is closed with the film member 12 (step S75).

By these operations, the optical probe 40 is contained and packed in the packing container 1.

Figure 8:
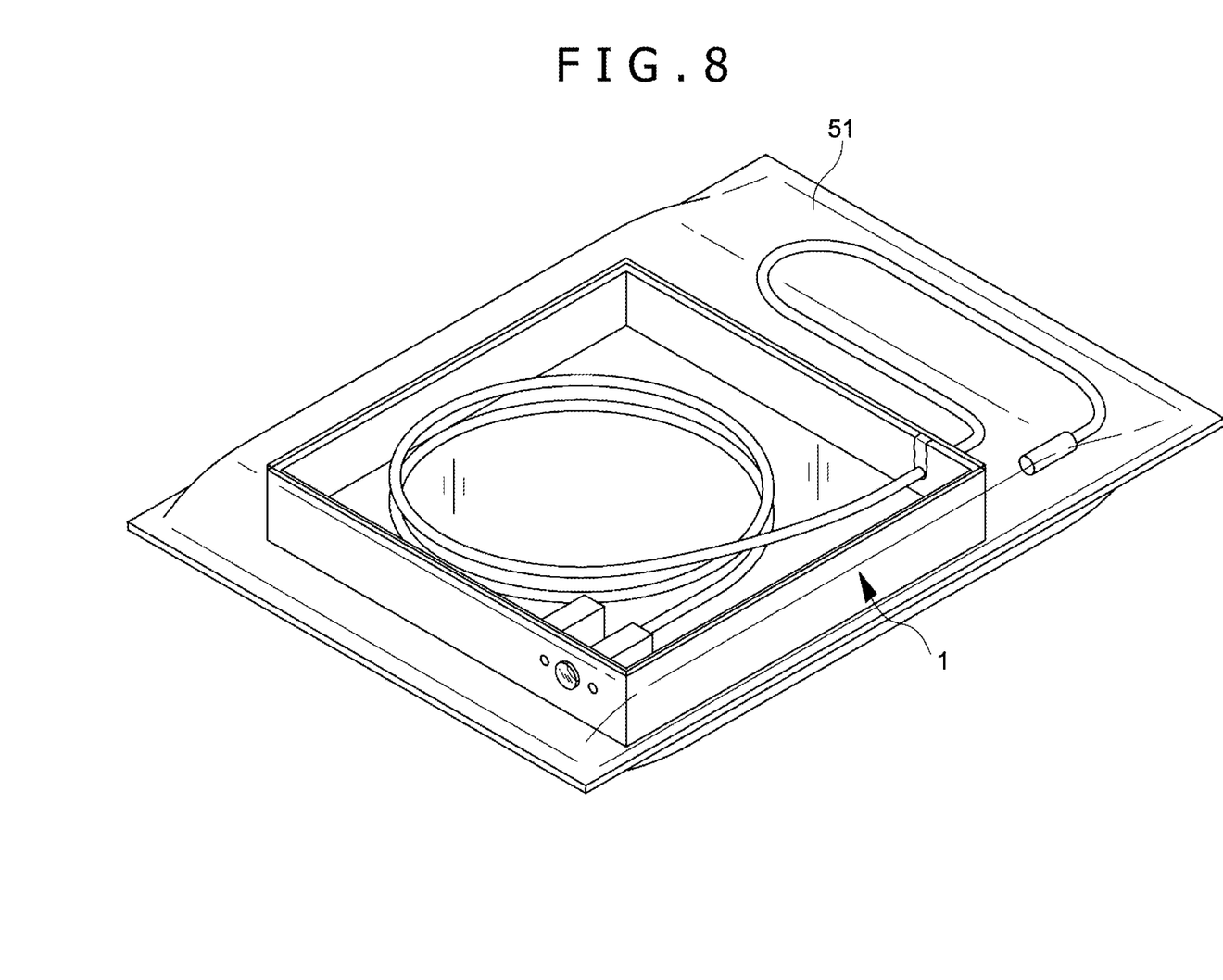
FIG. 8 illustrates a state in which the packing container shown in FIGS. 1 to 6 is put to secondary packing.

Subsequently, the operator put the packing container 1 to secondary packing (step S76). This is a process in which, as shown in FIG. 8, the packing container 1 is put into a bag 51 formed from thin film-shaped sheets, and the bag 51 is sealed off by putting an unsealing portion by thermocompression bonding or the like, whereby secondary packing is completed. As a material for the bag 51 formed from thin film-shaped sheets, a multi-layer film having PET (polyethylene terephthalate) as a base material can be used. Incidentally, as a method of sterilization for shipment, radiation sterilization is mainly used. Therefore, it is desirable that both the primary and secondary packing materials be high in radiation resistance. From this point of view, use of PP (polypropylene) or PVC (polyvinyl chloride) is not much desirable, in consideration of generation of gas (chlorine).

A multiplicity of the packing containers 1 having undergone secondary packing in the above-mentioned manner are, for example, stackedly contained in a corrugated fiberboard box (step S77). The multiplicity of the packing containers 1 contained in the corrugated fiberboard box are subjected to radiation sterilization or electron-beam sterilizing treatment, whereby sterilization of the inside and the outside of the packing containers 1 and sterilization of the inside of the secondary packing (bag 51) can be secured (step S78).

(Check of Output Intensity of Laser Beam)

Figure 9:
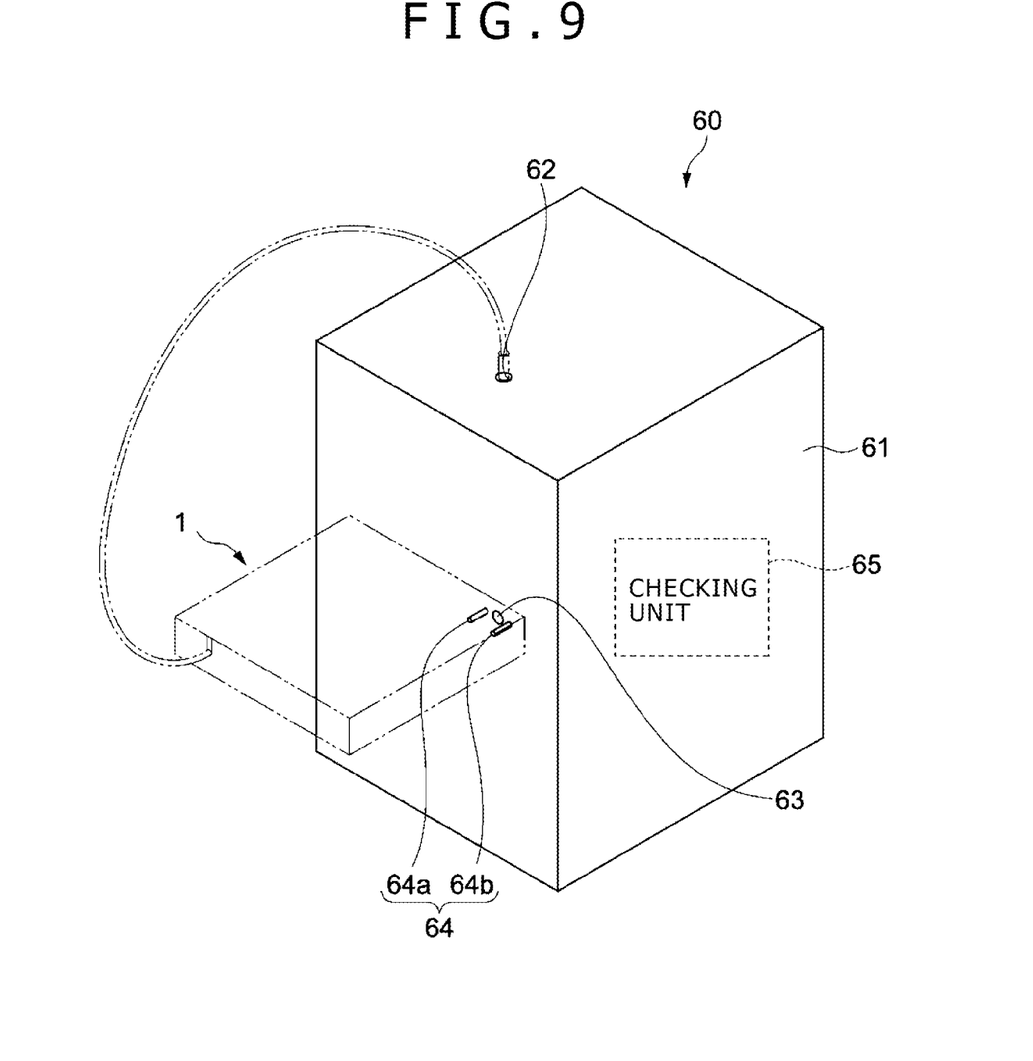
FIG. 9 illustrate a state in which the packing container shown in FIGS. 1 to 6 is mounted to a laser system.

FIG. 9 shows a state in which the packing container shown in FIGS. 1 to 6 is mounted to the laser system.

As shown in FIG. 9, the laser system 60 has a casing 61. The casing 61 is provided with a beam output port 62, an optical power meter 63, a positioning section 64, and a checking unit 65.

The beam output port 62 is for outputting a laser beam. The beam incoming section 42 which permits the laser beam to come in therethrough and which is led out from the packing container 1 is connected to the beam output port 62. The laser beam outputted from the beam output port 62 comes into the beam incoming section 42, and is transmitted through the optical probe body 41, to be let go out via the beam outgoing section 43.

The laser beam left go out from the beam outgoing section 43 of the optical probe 40 contained in the packing container 1 and transmitted through the window section 18 comes into the optical power meter 63. The optical power meter 63 measures the output intensity of the laser beam which comes thereinto.

The positioning section 64 is provided, at that position of the casing 61 which corresponds to the positioning section 19 provided in the packing container 1, with projections 64*a* and 64*b* for engagement with the recesses 19*a* and 19*b* provided at the positioning section 19. By the engagement of the recesses 19*a*, 19*b* with the projections 64*a*, 64*b*, the positional relationship between the beam outgoing section 43 of the optical probe 40 and the optical power meter 63 is determined. In other words, when the recesses 19*a* and 19*b* are engaged with these projections 64*a* and 64*b*, the window section 18 of the packing container 1 is positioned in a proper position in relation to the optical power meter 63 of the laser system 60.

The checking unit 65 checks the output intensity of the laser beam coming in through the optical power meter 63. For example, when the output intensity of the laser beam is not within a predetermined range, the checking unit 65 informs the operator of this situation by a sound or a display (indication), and stops the output of the laser beam from the beam output port 62. Or, alternatively, the checking unit 65 may calibrate the output of the laser beam from the beam output port 62 so that the output of the laser beam is within a predetermined range.

In the laser system 60 configured as above, the output intensity of the laser beam is checked in the following manner.

First, the operator connects the beam incoming section 42, led out from the packing container 1, to the beam output port 62 of the laser system 60.

Next, the operator puts the recesses 19*a*, 19*b* provided in the packing container 1 into engagement with the projections 64*a*, 64*b* provided in the laser system 60. As a result, the window section 18 of the packing container 1 is positioned in a proper position in relation to the optical power meter 63 of the laser system 60.

Subsequently, a laser beam is outputted from the beam output port 62, whereon the laser beam going out from the beam outgoing section 43 of the optical probe 40 contained in the packing container 1 comes into the optical power meter 63 of the laser system 60.

Then, the output intensity of the laser beam thus coming in via the optical power meter 63 is checked by the checking unit 65. For example, when the output intensity of the laser beam is not within a predetermined range, the laser system 60 informs the operator of this situation by a sound or a display (indication).

(Operation and Effect of Embodiment)

According to the present embodiment, with the optical probe 40 kept contained in the packing container 1, the laser beam from the beam outgoing section 43 can be let come into the optical power meter 63 of the laser system 60 through the window section 18 of the packing container 1. In other words, owing to the presence of the window section 18 provided in the packing container 1, checking of the output intensity of the laser beam can be conducted while keeping the sterility of the beam outgoing section 43 (while keeping the beam outgoing section 43 protected by the packing container 1); thus, cleanliness (hygiene) can be secured in a reliable manner. In addition, the need for an interface member such as an applicator is eliminated, so that checking of the output intensity of the laser beam can be carried out without spoiling workability. Besides, since a tip portion of the beam outgoing section 43 is held in the packing container 1, the tip portion can be prevented from being damaged during transportation.

According to the present embodiment, when the recesses 19*a* and 19*b* of the packing container 1 are engaged with the projections 64*a* and 64*b* of the laser system 60, the window section 18 is positioned in a proper position in relation to the optical power meter 63 of the laser system 60; therefore, the packing container 1 can be fixed relative to the laser system 60 as designed, independently of whether the operator is skilled or not. Specifically, since the tip portion of the beam outgoing section 43 is held in the packing container 1, when the packing container 1 is fixed onto the laser system 60 as above-mentioned, the packing container 1 can be disposed in the position as designed, so that checking of the output intensity of the laser beam can be carried out in a stable manner, independently of whether the operator is skilled or not.

(Other Embodiments)

Figure 10:
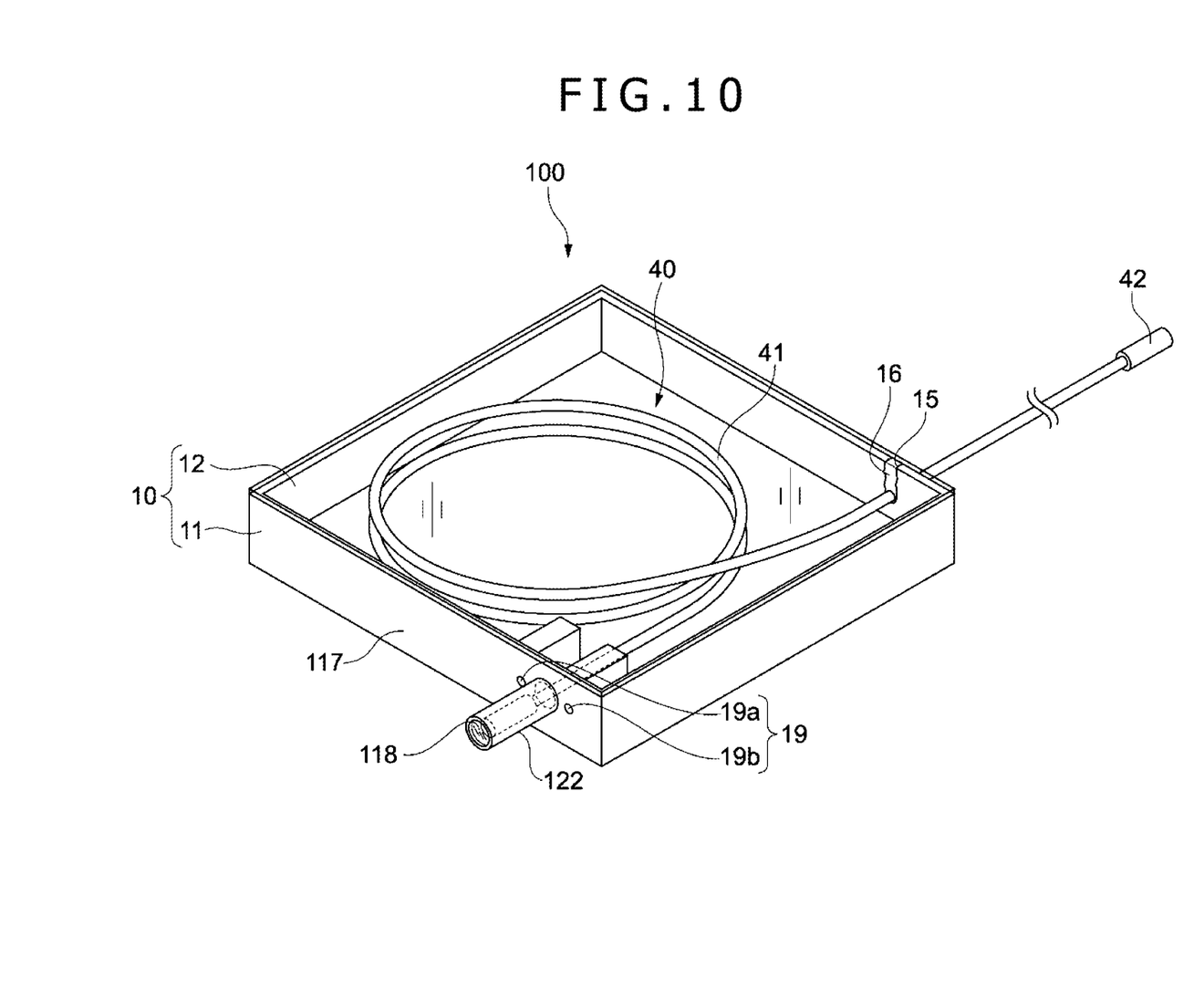
FIG. 10 is a perspective view showing the configuration of a packing container for an optical probe according to a second embodiment of the present technology.

FIG. 10 is a perspective view showing the configuration of a packing container according to a second embodiment of the present technology.

As shown in FIG. 10, the packing container 100 according to the second embodiment differs from the packing container 1 of the first embodiment in that a window section 118 is provided at a tip face part of a projected section 122 projected from a second side surface 117. Incidentally, in FIG. 10, the other components are denoted by the reference symbols used for those (same components) in the first embodiment.

In the packing container 100 in the second embodiment, the window section 118 is provided at the tip face part of the projected section 122, whereby the optical power meter of the laser system can be provided at a bottom part of a recessed section. This ensures that protection of the optical power meter and positioning between the window section and the optical power meter can be carried out more accurately.

Figure 11:
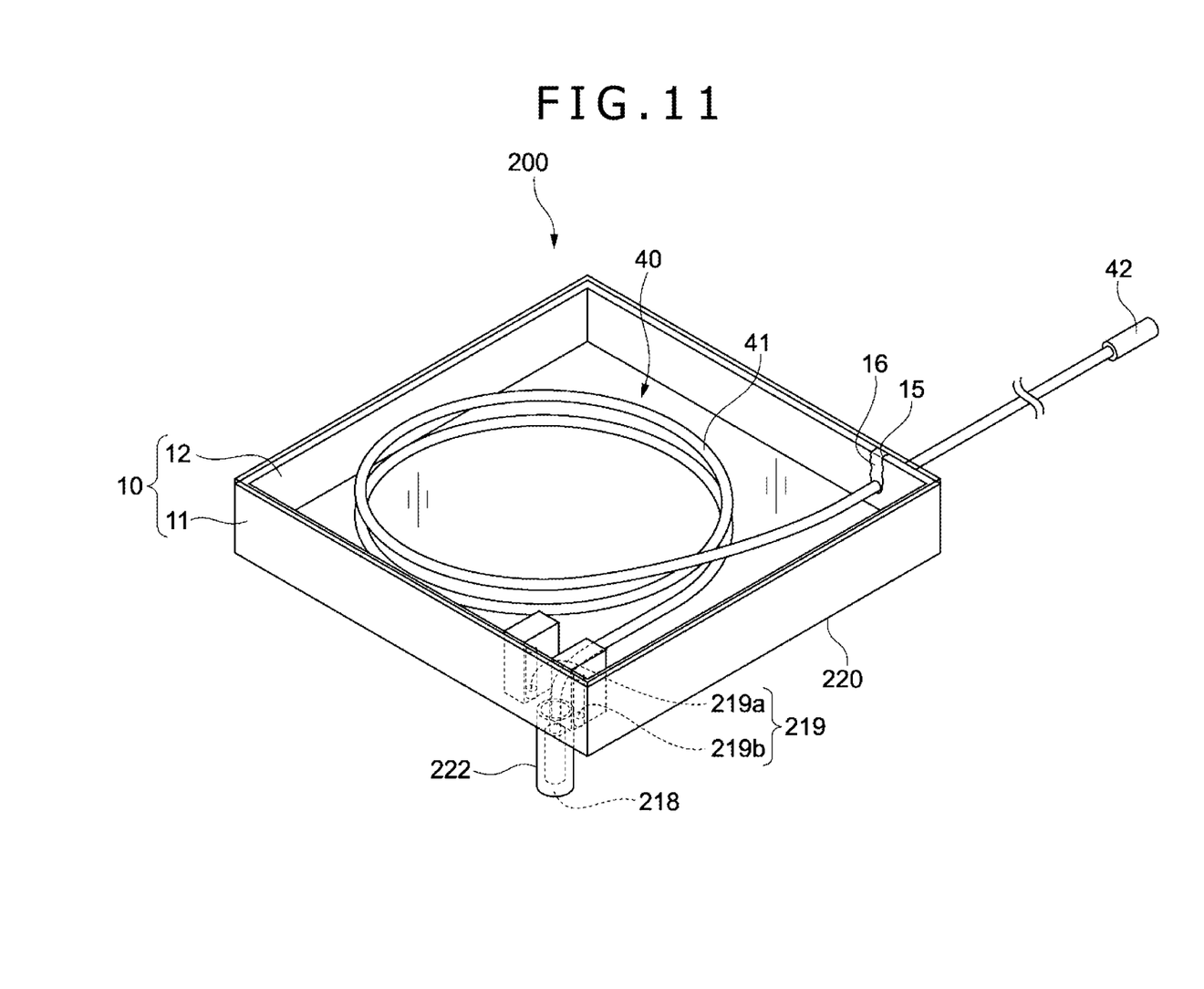
FIG. 11 is a perspective view showing the configuration of a packing container for an optical probe according to a third embodiment of the present technology.
Figure 12:
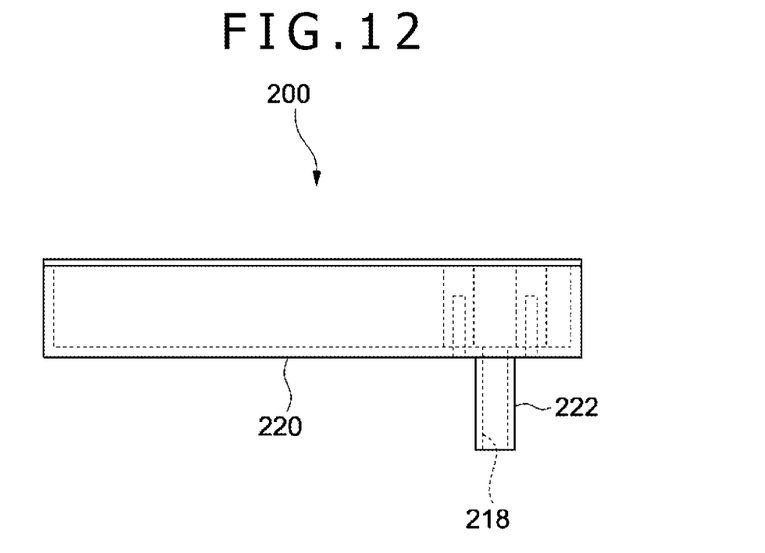
FIG. 12 is a side view of FIG. 11.

FIG. 11 is a perspective view showing the configuration of a packing container according to a third embodiment of the present technology. FIG. 12 is a side view of FIG. 11.

As shown in FIGS. 11 and 12, the packing container 200 according to the third embodiment differs from the packing container 1 in the first embodiment in that a window section 218 is provided at a tip face part of a projected section 222 projected to the exterior from a floor surface 220. In addition, the packing container 200 differs from the packing container 1 also in that the floor surface 220 is provided with a recessed section 219 (219a, 219b). Incidentally, in FIG. 11, the other components are denoted by the reference symbols used for those (same components) in the first embodiment.

In the packing container 200 in the third embodiment, the window section 218 is provided at the tip face part of the projected section 222 projected to the exterior from the floor surface 220, whereby the packing container 200 can be made substantially smaller in projection area than the packing container 100 according to the second embodiment.

Incidentally, the present technology is not restricted to the above-described embodiments.

Figure 13:
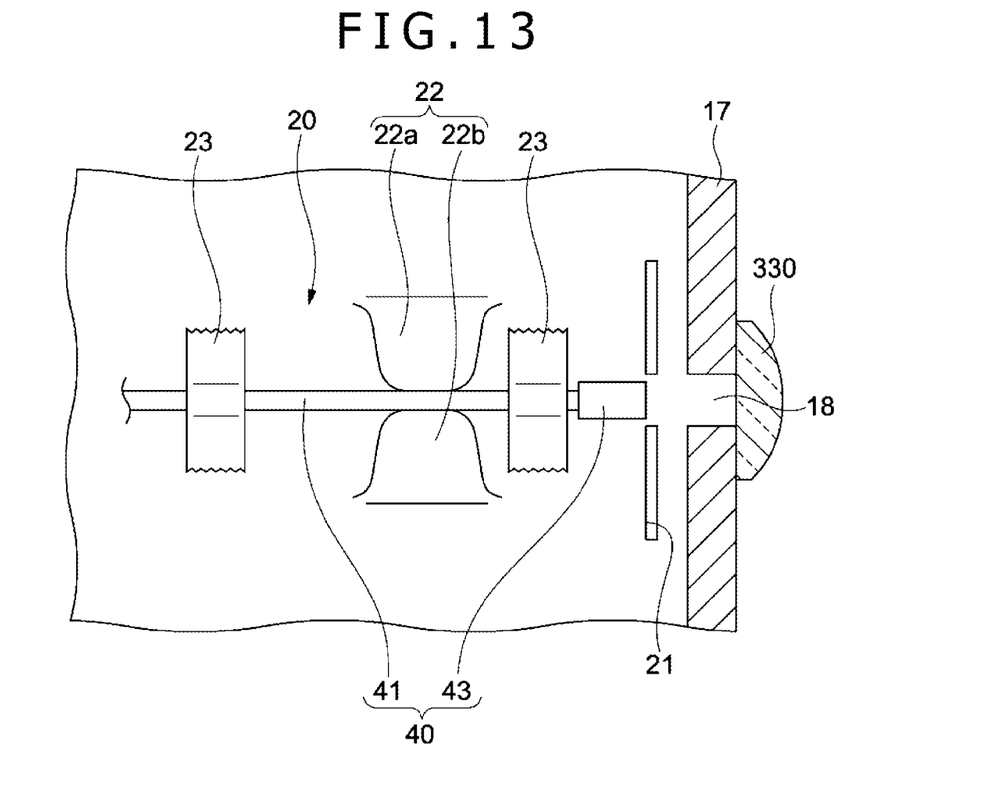
FIG. 13 is a partial enlarged plan view showing a modification of the present technology.

For example, as shown in FIG. 13, as a light-transmitting member 330, there may be used a convex lens by which the laser beam outputted to the exterior can be made to be parallel beam. When such a convex lens is used, the area of a light receiving surface of, for example, a photodetector on the optical power meter side can be reduced. In addition, the allowable range for misalignment between the window section and the optical power meter can be broadened.

Figure 14:
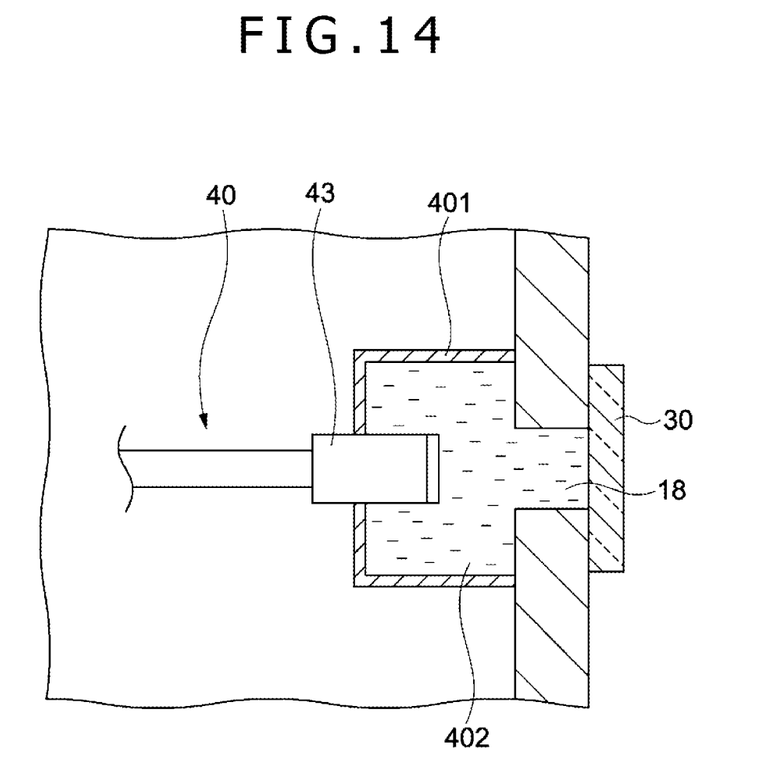
FIG. 14 is a partial enlarged plan view showing another modification of the present technology.

Besides, as shown in FIG. 14, a wall 401 by which the region between an end face of the beam outgoing section 43 of the optical probe 40 and the window section 18 (the light-transmitting member 30) is partitioned from the other region may be provided, and the region partitioned by the wall 401 may be filled with, for example, physiological saline 402. With the physiological saline 402 intermediately provided between the end face of the beam outgoing section 43 of the optical probe 40 and the window section 18 (the light-transmitting member 30), the end face of the beam outgoing section 43 of the optical probe 40 and the light-transmitting member 30 can be cooled. This makes it possible to reduce the loss of the laser beam at the end face of the beam outgoing section 43 of the optical probe 40 and the light-transmitting member 30.

It should be understood that various changes and modifications to the presently preferred embodiments described herein will be apparent to those skilled in the art. Such changes and modifications can be made without departing from the spirit and scope and without diminishing its intended advantages. It is therefore intended that such changes and modifications be covered by the appended claims.

The application is claimed as follows:

1. A packing container comprising:
    a packing container body including an optical probe containing box and a film member designed to close an open side of the optical probe containing box, the optical probe containing box including:
    a leading-out section through which a beam incoming section of an optical probe is led out from the packing container to the exterior and which is sealed;
    a window section through which a laser beam from a beam outgoing section of the optical probe is led out to the exterior;
    a positioning section for positioning of the window section and a laser beam input section of a laser system to which the window section and the packing container are mounted, the positioning section having recesses provided respectively on both sides of the window section; and
    a light-transmitting member designed to close the window section and permit the laser beam to pass through, wherein the light-transmitting member is a flat plate-shaped member and is adhered to the optical probe containing box.

2. The packing container according to claim 1, wherein the optical probe containing box is rectangular in shape and has the open side on the upper side of the box.

3. The packing container according to claim 2, wherein the optical probe containing box has a first surface provided with the positioning section for positioning of both the window section and the laser beam input section of a laser system to which the window section and the packing container are mounted.

4. The packing container according to claim 3, wherein the optical probe containing box has a second surface which is opposed to the first surface and which is provided with the leading-out section at a position corresponding to the window section.

5. A method of packing an optical probe, the optical probe having a first end section for incoming of a laser beam and a second end section for outgoing of the incoming laser beam, the method comprising:
    containing the optical probe in a containing box, which has an open side, a leading-out section, and a window section closed with a light-transmitting member permitting a laser beam to pass through, in such a manner that the first end section is led out to the exterior through the leading-out section and that the second end section is opposed to the window section with a predetermined spacing, wherein the light-transmitting member is a flat plate-shaped member and is adhered to the containing box;
    sealing the leading-out section with a sealing material;
    positioning the window section and a laser beam input section of a laser system to which the containing box is mounted by using a positioning section of the containing box, wherein the positioning section has recesses provided respectively on both sides of the window section such that the recesses are engaged with positioning projections provided in the laser system; and
    closing the open side with a film member.

6. A laser system comprising:
    a casing;
    an optical power meter which is mounted to the casing and which receives a laser beam coming therein from a beam outgoing section of an optical probe kept contained in a packing container, wherein the packing container comprises an optical probe containing box including:
    a window section through which a laser beam from the beam outgoing section of the optical probe is led out to the optical power meter;
    a positioning section for positioning of the window section and a laser beam input section of the laser system to which the window section and the packing container are mounted, the positioning section having recesses provided respectively on both sides of the window section; and
    a light-transmitting member designed to close the window section and permit the laser beam to pass through, wherein the light-transmitting member is a flat plate-shaped member and is adhered to the optical probe containing box;
    a positioning engaging section which is provided on the casing at a position corresponding to the positioning section provided on the packing container, in such a manner as to engage with the positioning section, and which determines the positional relationship between the beam outgoing section and the optical power meter; and a checking unit operable to check the output intensity of the laser beam coming in through the optical power meter.

7. A checking method comprising:

putting a container-side engaging section provided on a packing container into engagement with a positioning engaging section provided on a laser system;

letting in a laser beam, which comes from a beam outgoing section of an optical probe contained in the packing container, through an optical power meter of the laser system, the optical power meter being determined in positional relationship with the beam outgoing section of the optical probe by the engagement; and checking the output intensity of the laser beam coming in through the optical power meter, wherein the packing container comprises an optical probe containing box including:

a window section through which the laser beam from the beam outgoing section of the optical probe is led out to the optical power meter;

the container-side engaging section for positioning of the window section and a laser beam input section of the laser system to which the window section and the packing container are mounted, the container-side engaging section having recesses provided respectively on both sides of the window section; and a light-transmitting member designed to close the window section and permit the laser beam to pass through, wherein the light-transmitting member is a flat plate-shaped member and is adhered to the optical probe containing box.

* * * * *